US011578356B2

(12) United States Patent
Light et al.

(10) Patent No.: US 11,578,356 B2
(45) Date of Patent: Feb. 14, 2023

(54) MATRIX ARRAYS AND METHODS FOR MAKING SAME

(71) Applicant: LIFE TECHNOLOGIES CORPORATION, Carlsbad, CA (US)

(72) Inventors: David Light, Branford, CT (US); Wolfgang Hinz, Killingworth, CT (US); Ronald Cicero, Menlo Park, CA (US); Christina Inman, San Mateo, CA (US); Paul Kenney, Sunnyvale, CA (US); Alexander Mastroianni, Alameda, CA (US); Roman Rozhkov, Carlsbad, CA (US); Yufang Wang, San Carlos, CA (US); Jeremy Gray, Larkspur, CA (US); Marc Glazer, San Jose, CA (US); Dmitriy Gremyachinskiy, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 266 days.

(21) Appl. No.: 16/938,192

(22) Filed: Jul. 24, 2020

(65) Prior Publication Data

US 2020/0354780 A1 Nov. 12, 2020

Related U.S. Application Data

(63) Continuation of application No. 16/120,007, filed on Aug. 31, 2018, now Pat. No. 10,738,353, which is a continuation of application No. 14/774,662, filed as application No. PCT/US2014/026735 on Mar. 13, 2014, now Pat. No. 10,066,260.

(60) Provisional application No. 61/858,977, filed on Jul. 26, 2013, provisional application No. 61/781,016, filed on Mar. 14, 2013.

(51) Int. Cl.
*C12Q 1/6837* (2018.01)
*C12Q 1/6869* (2018.01)
*C12Q 1/6834* (2018.01)
*C12Q 1/6806* (2018.01)

(52) U.S. Cl.
CPC ......... *C12Q 1/6837* (2013.01); *C12Q 1/6806* (2013.01); *C12Q 1/6834* (2013.01); *C12Q 1/6869* (2013.01)

(58) Field of Classification Search
CPC .. C12Q 1/6837; C12Q 1/6806; C12Q 1/6834; C12Q 1/6869
See application file for complete search history.

(56) References Cited

U.S. PATENT DOCUMENTS

| 4,806,287 | A | 2/1989 | Sulci et al. |
|---|---|---|---|
| 6,656,725 | B2 | 12/2003 | Mirzabekov et al. |
| 10,066,260 | B2 | 9/2018 | Light et al. |
| 2003/0003609 | A1 | 1/2003 | Sauer et al. |
| 2003/0064507 | A1 | 4/2003 | Gallagher et al. |
| 2005/0075482 | A1 | 4/2005 | Tanaka et al. |
| 2005/0233363 | A1* | 10/2005 | Harding ............. C12N 15/1072 435/6.16 |
| 2008/0166727 | A1 | 7/2008 | Esfandyarpour et al. |
| 2009/0127589 | A1 | 5/2009 | Rothberg et al. |
| 2010/0311127 | A1 | 12/2010 | Piepenburg et al. |
| 2011/0318820 | A1 | 12/2011 | Hinz et al. |
| 2013/0116153 | A1* | 5/2013 | Bowen ................ C12Q 1/6844 506/26 |
| 2013/0225421 | A1 | 8/2013 | Li et al. |
| 2013/0345088 | A1 | 12/2013 | Noji et al. |
| 2014/0228245 | A1 | 8/2014 | Hoffmann et al. |
| 2014/0243224 | A1* | 8/2014 | Barnard ............... B01J 19/0046 506/26 |

FOREIGN PATENT DOCUMENTS

| AU | 2012226920 B2 | 2/2015 |
|---|---|---|
| CN | 101413034 B | 2/2011 |
| WO | WO-200060919 A2 | 10/2000 |
| WO | WO-2005007796 A2 | 1/2005 |
| WO | WO-2005065814 A1 | 7/2005 |
| WO | WO-2010138187 A1 | 12/2010 |
| WO | WO-2012083189 A2 | 6/2012 |
| WO | WO-2013006824 A2 | 1/2013 |

OTHER PUBLICATIONS

Barbey et al., "Protein Microarrays Based on Polymer Brushes Prepared via Surface-Initiated Atom Transfer Radical Polymerization", Biomacromolecules, vol. 11, No. 12, Dec. 13, 2010, pp. 3467-3479.
EP17178012.5, Search Report, dated Nov. 20, 2017.
EP17181624.2, Search Report, dated Sep. 21, 2017.
Hucknall et al., "In Pursuit of Zero: Polymer Brushes that Resist the Adsorption of Proteins", Advanced Materials vol. 21, No. 23, Jun. 19, 2009, pp. 2441-2446.
PCT/US2014/026735 , Search Report and Written Opinion, dated Sep. 5, 2014.
Limpoco et al., "Real-Time Monitoring of Surface-Initiated Atom Transfer Radical Polymerization Using Silicon Photonic Microing Resonators: Implications for Combinatorial Screening of Polymer Brush Growth Conditions", Journal of the American Chemical Society, vol. 133, No. 38, Sep. 28, 2011, pp. 14864-14867.

(Continued)

*Primary Examiner* — Narayan K Bhat

(57) ABSTRACT

A method of forming a polymer matrix array includes treating a surface within a well of a well array with a surface compound including a surface reactive functional group and a radical-forming distal group; applying an aqueous solution including polymer precursors to the well of the well array; and activating the radical-forming distal group of the surface coupling compound with an initiator and atom transfer radical polymerization (ATRP) catalyst to initiate radical polymerization of the polymer precursors within the well of the well array to form the polymer matrix array.

20 Claims, 5 Drawing Sheets

(56) References Cited

OTHER PUBLICATIONS

Ma et al., "Protein-Resistant Polymer Coatings on Silicon Oxide by Surface-Initiated Atom Transfer Radical Polymerization", Lanqmuir vol. 22, 2006, pp. 3751-3756.
Morrison et al., "Nanoliter High Throughput Quantitative PCR", Nucleic Acids Research. vol. 34, No. 18, e123, 2006, 1-9.
neb.com, "DNA Polymerase Selection Chart", retrieved from internet URL:https://www.neb.com/tools-and-resources/selection-charts/dna-polymerase-selection-chart, Jul. 1, 2016, 5 pp.
PCT/US2014/026735, Partial Search Report, dated Jun. 25, 2014.
Piepenburg et al., "DNA Detection Using Recombination Proteins", PLoS Biology, vol. 4, Issue 7, e204, 2006, pp. 1115-1121.
Rehman et al., "Immobilization of Acrylamide-modified Oligonucleotides by Copolymerization", Nucleic Acids Research, vol. 27, No. 2, 1999, pp. 649-655.
SG11201406717R, Written Opinion, dated Nov. 24, 2015.
Xu et al., "Simultaneous amplification and screening of whole plasmids using the T7 bacteriophage replisome", Nucleic Acid Research, vol. 34, No. 13, 2006, p. e98 (9 pages).

\* cited by examiner

MATRIX ARRAYS AND METHODS FOR MAKING SAME

CROSS-REFERENCE TO RELATED APPLICATION(S)

This application is a continuation of U.S. application Ser. No. 16/120,007 filed Aug. 31, 2018, which is a continuation of U.S. application Ser. No. 14/774,662 filed Mar. 13, 2014 (now U.S. Pat. No. 10,066,260), which is a U.S. National Application filed under 35 U.S.C. 371 of PCT Application No. PCT/US2014/026735 filed Mar. 13, 2014, which application claims benefit under 35 U.S.C. 119(e) of U.S. Provisional Application No. 61/781,016 filed Mar. 14, 2013, and claims benefit under 35 U.S.C. 119(e) of U.S. Provisional Application No. 61/858,977, filed Jul. 26, 2013. The entire contents of the aforementioned applications are incorporated by reference herein.

FIELD OF THE DISCLOSURE

This disclosure, in general, relates to matrix arrays defining reaction volumes and methods for forming such matrix arrays.

BACKGROUND

Increasingly, arrays of small volume polymer matrices are of interest to researchers in fields such as analytical chemistry and molecular biology. These small volume polymer matrices can be used to capture analytes and perform analysis in dilute systems or can be used to perform analysis of multiple analytes simultaneously. In particular, these polymer matrix arrays can be useful for genetic sequencing techniques.

Older techniques of genetic sequencing, such as Sanger sequencing, have proven expensive and time consuming. More recently, bead arrays have been explored for fluorescent-based sequencing techniques. However, such techniques suffer from difficulties associated with capturing target polynucleotides to be sequenced and retaining such target polynucleotides within a resolvable reaction volume during sequencing. Further, practitioners report difficulties associated with preparation of the beads and bead arrays.

SUMMARY

In an embodiment, polymer matrix precursors can be applied to an array of wells associated with one or more sensors. The polymer matrix precursors can be polymerized to form an array of polymer matrices. These polymer matrices can be conjugated to oligonucleotides and can be useful in various analytical techniques including genetic sequencing techniques.

BRIEF DESCRIPTION OF THE DRAWINGS

The present disclosure may be better understood, and its numerous features and advantages made apparent to those skilled in the art by referencing the accompanying drawings.

The use of the same reference symbols in different drawings indicates similar or identical items.

DETAILED DESCRIPTION

Figure 1:
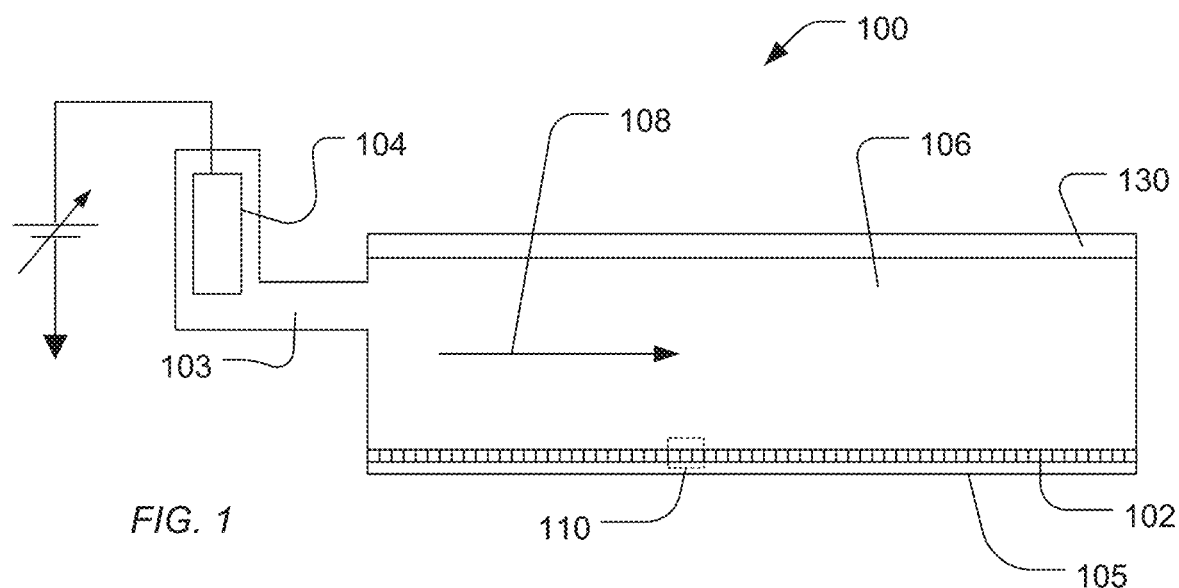
FIG. 1 includes an illustration of an exemplary measurement system.

In an exemplary embodiment, a measurement system includes an array of hydrophilic polymer matrices distributed in wells associated with sensors, such as sensors of a sensor array. In an example, the hydrophilic matrices are hydrogel matrices. The hydrophilic matrices can correspond with sensors of the sensor array in a one-to-one configuration. In a further example, the sensors of the sensor array can include field effect transistor (FET) sensors, such as ion sensitive field effect transistors (ISFET). In particular, the matrix material is cured-in-place and conforms to the configuration of individual wells of a sensing device. The interstitial areas between the wells can be substantially free of the polymer matrix. In an example, the matrix material can be bonded, such as covalently bonded, to a surface of the wells. In an example, the wells have a depth or thickness in a range of 100 nm to 10 micrometers. In another example, the wells can have a characteristic diameter in a range of 0.1 micrometers to 2 micrometers.

In an exemplary method, the polymer matrix array can be formed by applying an aqueous solution including polymer precursors into wells of a well array. Volumes of the aqueous material defined by the well array can be isolated using an immiscible fluid disposed over the well array. The isolated volumes of the solution can be initiated to facilitate polymerization of the matrix precursors, resulting in a matrix array distributed within the wells. In an example, an aqueous solution including matrix precursors is distributed to the wells of the sensing device by flowing the aqueous precursor over the wells. In another example, the aqueous solution is included as a dispersed phase within an emulsion. The dispersed phase can settle or be motivated into wells of the well array. The polymerization of the matrix precursors can be initiated using initiators disposed within the aqueous phase or within the immiscible fluid. In another example, the polymerization can be initiated thermally.

In another exemplary method, a matrix array can be formed within wells of a sensing device by anchoring initiator molecules to a surface within wells of the well array. The solution including matrix precursors can be provided over the wells of the well array. An initiator can initiated polymerization of the matrix precursors, resulting in the formation of the polymer matrix within wells of the well array. In a further example, aspects of the above methods can be combined to further enhance formation of the matrix arrays.

In a particular example, a sequencing system includes a flow cell in which a sensory array is disposed, includes communication circuitry in electronic communication with the sensory array, and includes containers and fluid controls in fluidic communication with the flow cell. In an example, FIG. 1 illustrates an expanded and cross-sectional view of a flow cell 100 and illustrates a portion of a flow chamber 106.

A reagent flow 108 flows across a surface of a well array 102, in which the reagent flow 108 flows over the open ends of wells of the well array 102. The well array 102 and a sensor array 105 together can form an integrated unit forming a lower wall (or floor) of the flow cell 100. A reference electrode 104 can be fluidically coupled to flow chamber 106. Further, a flow cell cover 130 encapsulates flow chamber 106 to contain reagent flow 108 within a confined region.

Figure 2:
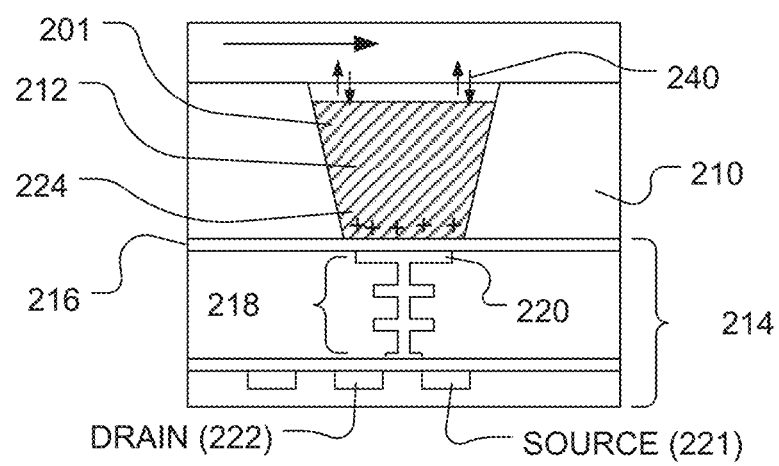
FIG. 2 includes an illustration of an exemplary measurement component.

FIG. 2 illustrates an expanded view of a well 201 and a sensor 214, as illustrated at 110 of FIG. 1. The volume, shape, aspect ratio (such as base width-to-well depth ratio), and other dimensional characteristics of the wells can be selected based on the nature of the reaction taking place, as well as the reagents, byproducts, or labeling techniques (if any) that are employed. The sensor 214 can be a chemical field-effect transistor (chemFET), more specifically an ion-sensitive FET (ISFET), with a floating gate 218 having a sensor plate 220 optionally separated from the well interior by a material layer 216. In addition, a conductive layer (not illustrated) can be disposed over the sensor plate 220. In an example, the material layer 216 includes an ion sensitive material layer. The material layer 216 can be a ceramic layer, such as an oxide of zirconium, hafnium, tantalum, aluminum, or titanium, among others, or a nitride of titanium. Alternatively, the metal layer or the material layer 216 can be formed of a metal, such as titanium, tungsten, gold, silver, platinum, or a combination thereof. In an example, the material layer 216 can have a thickness in a range of 5 nm to 100 nm, such as a range of 10 nm to 70 nm, a range of 15 nm to 65 nm, or even a range of 20 nm to 50 nm.

While the material layer 216 is illustrated as extending beyond the bounds of the illustrated FET component, the material layer 216 can extend along the bottom of the well 201 and optionally along the walls of the well 201. The sensor 214 can be responsive to (and generate an output signal related to) the amount of a charge 224 present on material layer 216 opposite the sensor plate 220. Changes in the charge 224 can cause changes in a current between a source 221 and a drain 222 of the chemFET. In turn, the chemFET can be used directly to provide a current-based output signal or indirectly with additional circuitry to provide a voltage-based output signal. Reactants, wash solutions, and other reagents can move in and out of the wells by a diffusion mechanism 240.

In an embodiment, reactions carried out in the well 201 can be analytical reactions to identify or determine characteristics or properties of an analyte of interest. Such reactions can generate directly or indirectly byproducts that affect the amount of charge adjacent to the sensor plate 220. If such byproducts are produced in small amounts or rapidly decay or react with other constituents, multiple copies of the same analyte can be analyzed in the well 201 at the same time in order to increase the output signal generated. In an embodiment, multiple copies of an analyte can be attached to a solid phase support 212, either before or after deposition into the well 201. The solid phase support 212 can be a polymer matrix, such as a hydrophilic polymer matrix, for example, a hydrogel matrix or the like. For simplicity and ease of explanation, solid phase support 212 is also referred herein as a polymer matrix.

The well 201 can be defined by a wall structure, which can be formed of one or more layers of material. In an example, the wall structure can have a thickness extending from the lower surface to the upper surface of the well in a range of 0.01 micrometers to 10 micrometers, such as a range of 0.05 micrometers to 10 micrometers, a range of 0.1 micrometers to 10 micrometers, a range of 0.3 micrometers to 10 micrometers, or a range of 0.5 micrometers to 6 micrometers. In particular, the thickness can be in a range of 0.01 micrometers to 1 micrometer, such as a range of 0.05 micrometers to 0.5 micrometers, or a range of 0.05 micrometers to 0.3 micrometers. The wells 201 can have a characteristic diameter, defined as the square root of 4 times the cross-sectional area (A) divided by Pi (e.g., sqrt(4*A/π), of not greater than 5 micrometers, such as not greater than 3.5 micrometers, not greater than 2.0 micrometers, not greater than 1.6 micrometers, not greater than 1.0 micrometers, not greater than 0.8 micrometers or even not greater than 0.6 micrometers. In an example, the wells 201 can have a characteristic diameter of at least 0.01 micrometers. In a further example, the well 201 can define a volume in a range of 0.05 fL to 10 pL, such as a volume in a range of 0.05 fL to 1 pL, a range of 0.05 fL to 100 fL, a range of 0.05 fL to 10 fL, or even a range of 0.1 fL to 5 fL.

While FIG. 2 illustrates a single-layer wall structure and a single-layer material layer 216, the system can include, one or more wall structure layers, one or more conductive layers or one or more material layers. For example, the wall structure can be formed of one or more layers, including an oxide of silicon or TEOS or including a nitride of silicon.

Figure 3:
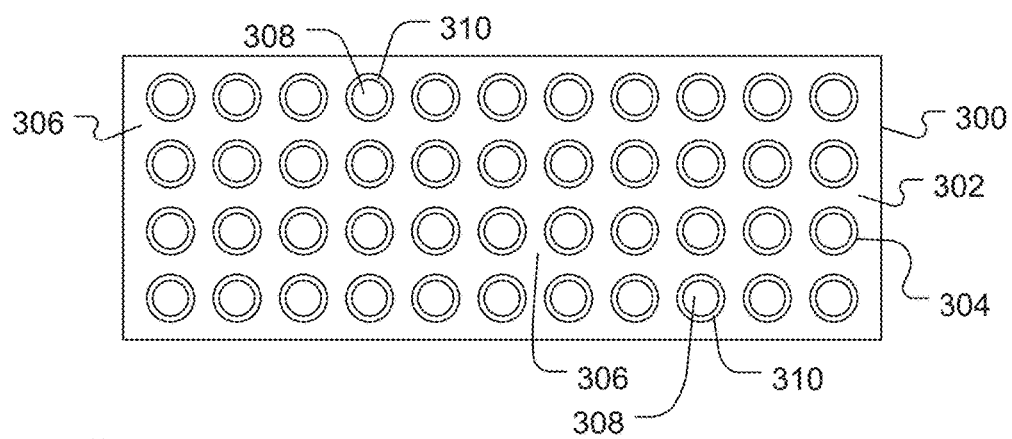
FIG. 3 includes an illustration of exemplary array of measurement components.

In a particular example illustrated in FIG. 3, a system 300 includes a well wall structure 302 defining an array of wells 304 disposed over or operatively coupled to sensor pads of a sensor array. The well wall structure 302 defines an upper surface 306. A lower surface 308 associated with the well is disposed over a sensor pad of the sensor array. The well wall structure 302 defines a sidewall 310 between the upper surface 306 and the lower surface 308. As described above, a material layer in contact with sensor pads of the sensor array can extend along the lower surface 308 of a well of the array of wells 304 or along at least a portion of the wall 310 defined by the well wall structure 302. The upper surface 306 can be free of the material layer. In particular, a polymer matrix can be disposed in the wells of the array of wells 304. In an example, the upper surface 306 can be substantially free of the polymer matrix. For example, the upper surface 306 can include an area that is free of the polymer matrix, such as at least 70% of the total area, at least 80% of the total area, at least 90% of the total area or approximately 100% of the total area.

Figure 4:
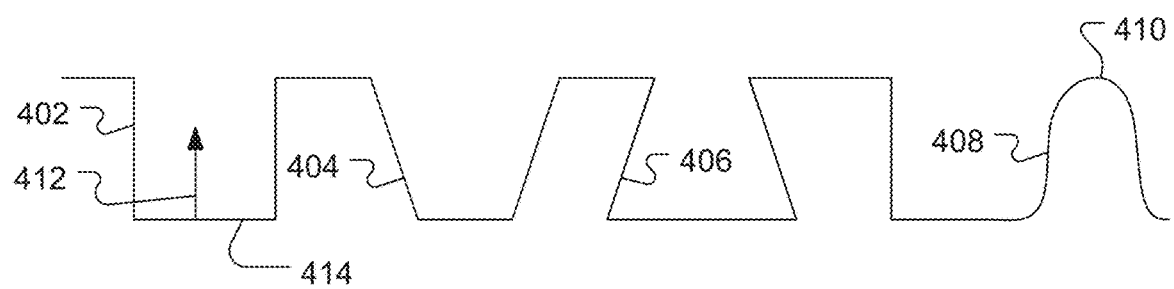
FIG. 4 includes an illustration of exemplary well configurations.

While the wall surface of FIG. 2 is illustrated as extending substantially vertically and outwardly, the wall surface can extend in various directions and have various shapes. Substantially vertically denotes extending in a direction having a component that is normal to the surface defined by the sensor pad. For example, as illustrated in FIG. 4, a well wall 402 can extend vertically, being parallel to a normal component 412 of a surface defined by a sensor pad. In another example, the wall surface 404 extends substantially vertically, in an outward direction away from the sensor pad, providing a larger opening to the well than the area of the lower surface of the well. As illustrated in FIG. 4, the wall surface 404 extends in a direction having a vertical component parallel to the normal component 412 of the surface 414. In an alternative example, a wall surface 406 extends substantially vertically in an inward direction, providing an opening area that is smaller than an area of the lower surface of the well. The wall surface 406 extends in a direction having a component parallel to the normal component 412 of the surface 414.

While the surfaces 402, 404, or 406 are illustrated by straight lines, some semiconductor or CMOS manufacturing processes can result in structures having nonlinear shapes. In particular, wall surfaces, such as wall surface 408 and upper surfaces, such as upper surface 410, can be arcuate in shape or take various nonlinear forms. While the structures and devices illustrated herewith are depicted as having linear layers, surfaces, or shapes, actual layers, surfaces, or shapes resulting from semiconductor processing can differ to some degree, possibly including nonlinear and arcuate variations of the illustrated embodiment.

Figure 5:
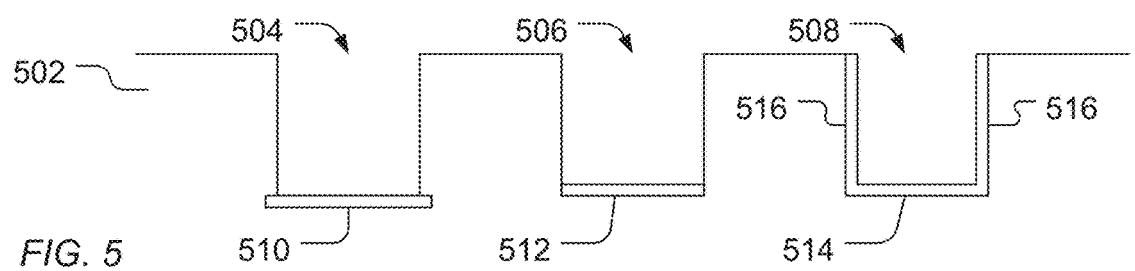
FIG. 5 includes an illustration of exemplary well and sensor configurations.

FIG. 5 includes an illustration of exemplary wells including ion sensitive material layers. For example, a well structure 502 can define an array of wells, such as exemplary wells 504, 506, or 508. The wells (504, 506, or 508) can be operatively coupled to an underlying sensor (not illustrated) or linked to such an underlying sensor. Exemplary well 504 includes an ion sensitive material layer 510 defining the bottom of the well 504 and extending into the structure 502. While not illustrated in FIG. 5, a conductive layer, such as a gate, for example, a floating gate of ion sensitive field effect transistor can reside below the ion sensitive material layer 510.

In another example, as illustrated by well 506, an ion sensitive material layer 512 can define the bottom of the well 506 without extending into the structure 502. In a further example, a well 508 can include an ion sensitive layer 514 that extends along at least a portion of a sidewall 516 of the well 508 defined by the structure 502. As above, the ion sensitive material layers 512 or 514 can reside over conductive layers or gates of underlying electronic devices.

Returning to FIG. 2, the matrix material 212 is conformal with the well structure. In particular, the matrix material can be cured in place to be conformal to the walls and bottom surface of the well. An upper surface through which the wells are defined can include an area that is substantially free of the matrix material. For example, at least 70% of the total area, at least 80% of the total area, at least 90% of the total area or approximately 100% of the total area can free of the matrix material. Depending upon the nature of the well structure, the polymer matrix can be physically secured to the well wall structure. In another example, the polymer matrix can be chemically bound to the well wall structure. In particular, the polymer matrix can be covalently bound to the well wall structure. In another example, the polymer matrix can be bound by hydrogen bonding or ionic bonding to the well wall structure.

The polymer matrix can be formed from matrix precursors, such as a radically polymerizable monomer, for example, a vinyl-based monomer. In particular, the monomer can include a hydrophilic monomer, such as an acrylamide, vinyl acetate, hydroxyalkylmethacrylate, variations or derivatives thereof, copolymers thereof, or any combination thereof. In a particular example, the hydrophilic monomer is an acrylamide, such as an acrylamide functionalized to include hydroxyl groups, amino groups, carboxyl groups, halogen groups, or a combination thereof. In an example, the hydrophilic monomer is an aminoalkyl acrylamide, an acrylamide functionalized with an amine terminated polyalkyl glycol (D, illustrated below), an acrylopiperazine (C, illustrated below), or a combination thereof. In another example, the acrylamide can be a hydroxyalkyl acrylamide, such as hydroxyethyl acrylamide. In particular, the hydroxyalkyl acrylamide can include N-tris(hydroxymethyl)methyl)acrylamide (A, illustrated below), N-(hydroxymethyl)acrylamide (B, illustrated below), or a combination thereof. The acrylamide functionalized with an amine terminated polyalkyl glycol can include between 1 and 20 units of an alkyl glycol, such as ethylene glycol, propylene glycol, or a combination thereof. In another example, a comonomer can include a halogen modified acrylate or acrylamide, such as a N-(5-bromoacetamidylpentyl)acrylamide (BRAPA, E, illustrated below). While BRAPA is illustrated as including a bromoacetamide group, a bromoalkylamide including an alkyl group of 2 to 20 carbons can be used. Further, the pentyl group of BRAPA can be replaced with another alkyl group having a carbon length in a range of 2 to 20. In another example, a comonomer can include an oligonucleotide modified acrylate or acrylamide monomer. In a further example, a mixture of monomers, such as a mixture of hydroxyalky acrylamide and amine functionalize acrylamide or a mixture of acrylamide and amine functionalized acrylamide, can be used. In an example, the amine functionalize acrylamide can be included in a ratio of hydroxyalkyl acrylamide:amine functionalized acrylamide or acrylamide:amine functionalized acrylamide in a range of 100:1 to 1:1, such as a range of 100:1 to 2:1, a range of 50:1 to 3:1, a range of 50:1 to 5:1 or even a range of 50:1 to 10:1. In another example, the amine functionalize acrylamide can be included in a ratio of hydroxyalkyl acrylamide:bromine functionalized acrylamide or acrylamide:bromine functionalized acrylamide in a range of 100:1 to 1:1, such as a range of 100:1 to 2:1, a range of 50:1 to 3:1, a range of 50:1 to 5:1 or even a range of 50:1 to 10:1.

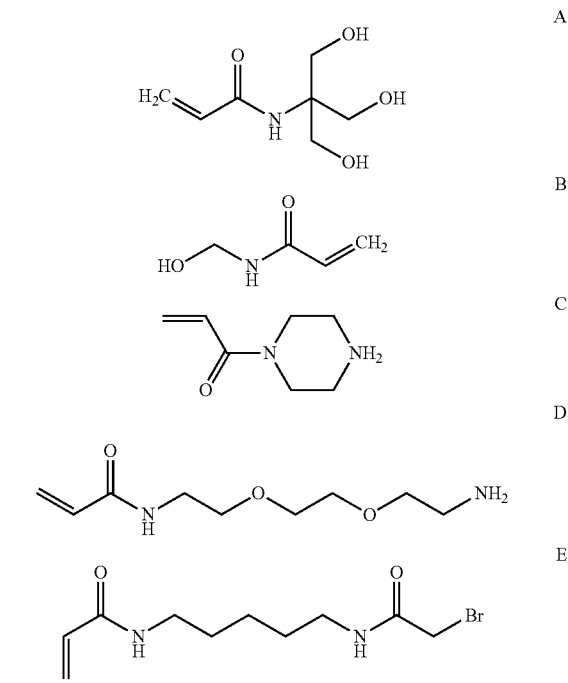

In a further example, an oligonucleotide functionalized acrylamide or acrylate monomer, such as an Acrydite™ monomer, can be included to incorporate oligonucleotides into the polymer matrix.

Another exemplary matrix precursor includes a crosslinker. In an example, the crosslinker is included in a mass ratio of monomer to crosslinker in a range of 15:1 to 1:2, such as a range of 10:1 to 1:1, a range of 6:1 to 1:1, or even a range of 4:1 to 1:1. In particular, the crosslinker can be a divinyl crosslinker. For example, a divinyl crosslinker can include a diacrylamide, such as N,N'-(ethane-1,2-diyl)bis(2-hydroxyl ethyl)acrylamide, N,N'-(2-hydroxypropane-1,3-diyl)diacrylamide, or a combination thereof. In another example, a divinyl crosslinker includes ethyleneglycol dimethacrylate, divinylbenzene, hexamethylene bisacrylamide, trimethylolpropane trimethacrylate, a protected derivative thereof, or a combination thereof.

In one aspect, polymer networks comprise polyacrylamide gels with total monomer percentages in the range of from 1 to 20 percent (e.g., 3 to 20 percent), and more preferably, in the range of from 2 to 10 percent, such as 5 to 10 percent. In one embodiment, crosslinker percentage of monomers is in the range of from 5 to 10 percent. In a particular embodiment, polymer networks comprise 2 to 10 percent total acrylamide of which 10 percent is bisacrylamide crosslinker.

Polymerization can be initiated by an initiator within the solution. For example, the initiator can be a water-based. In another example, the initiator can be a hydrophobic initiator, preferentially residing in a hydrophobic phase. An exemplary initiator includes ammonium persulfate and TEMED (tetramethylethylenediamine). TEMED can accelerate the rate of formation of free radicals from persulfate, in turn catalyzing polymerization. The persulfate free radicals, for example, convert acrylamide monomers to free radicals which react with unactivated monomers to begin the polymerization chain reaction. The elongating polymer chains can be randomly crosslinked, resulting in a gel with a characteristic porosity which depends on the polymerization conditions and monomer concentrations. Riboflavin (or riboflavin-5'-phosphate) can also be used as a source of free radicals, often in combination with TEMED and ammonium persulfate. In the presence of light and oxygen, riboflavin is converted to its leuco form, which is active in initiating polymerization, which is usually referred to as photochemical polymerization.

In another example, an azo initiator can be used to initiate polymerization. Exemplary water soluble azo initiators are illustrated in Table 1 and exemplary oil soluble azo initiators are illustrated in Table 2. In particular, the azo initiator can be azobisisobutyronitrile (AIBN).

TABLE I

Water Soluble Azo Initiator Compounds

| Structure | | 10 hour half-life decomposition temperature |
|---|---|---|
| 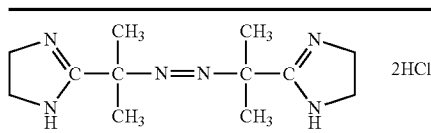 | 2HCl | 44° C. |
| 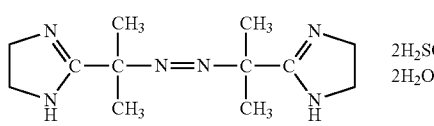 | 2H$_2$SO$_4$ 2H$_2$O | 47° C. |
| 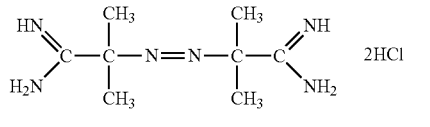 | 2HCl | 56° C. |
| 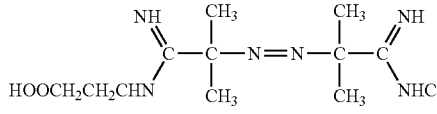 | 4H$_2$O | 57° C. |
| 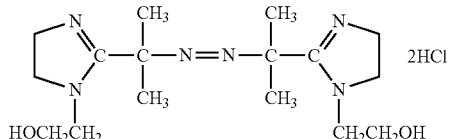 | 2HCl | 60° C. |
| 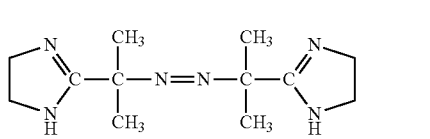 [SMILES: CC(C)(N=NC(C)(C)C1=NCCN1)C1=NCCN1] | | 61° C. |
| 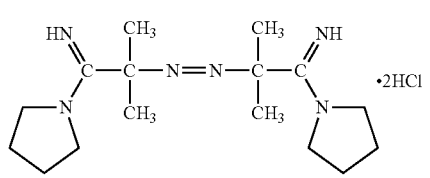 [SMILES: CC(C)(N=NC(C)(C)C(=N)N1CCCC1)C(=N)N1CCCC1] | ·2HCl | 67° C. |

TABLE I-continued

Water Soluble Azo Initiator Compounds

| Structure | 10 hour half-life decomposition temperature |
|---|---|
| HOH₂C–C(=O)–N(CHCH₂OH)(CH₂OH)–... –C(CH₃)₂–N=N–C(CH₃)₂–C(=O)–NHCH(CH₂OH)(CH₂OH) structure | 80° C. |
| HOH₂CH₂CHN–C(=O)–C(CH₃)₂–N=N–C(CH₃)₂–C(=O)–NHCH₂CH₂OH | 87° C. |

TABLE II

Oil Soluble Azo Initiator Compounds

| Structure | 10 hour half-life decomposition temperature |
|---|---|
| H₃CO–C(CH₃)(CH₂CCH₃H₃)–N=N–C(CH₃)(CH₂CCH₃H₃)–OCH₃ (dimethoxy structure) | 30° C. |
| H₃CHCH₂C(CH₃)(CN)–N=N–C(CN)(CH₃)–CH₂CHCH₃ | 51° C. |
| H₃CO–C(=O)–C(CH₃)₂–N=N–C(CH₃)₂–C(=O)–OCH₃ | 66° C. |
| H₃CH₂C–C(CH₃)(CN)–N=N–C(CN)(CH₃)–CH₂CH₃ | 67° C. |
| Bis(1-cyanocyclohexyl)diazene | 88° C. |
| H₂C=HCH₂CHN–C(=O)–C(CH₃)₂–N=N–C(CH₃)₂–C(=O)–NHCH₂CH=CH₂ | 96° C. |
| H₃C–C(CH₃)(CN)–N=N–CONH₂ | 104° C. |
| H₃CH₂CH₂CH₂CHN–C(=O)–C(CH₃)₂–N=N–C(CH₃)₂–C(=O)–NHCH₂CH₂CH₂CH₃ | 110° C. |

TABLE II-continued

Oil Soluble Azo Initiator Compounds

| Structure | 10 hour half-life decomposition temperature |
|---|---|
| [Structure: cyclohexyl-NH-C(=O)-C(CH₃)₂-N=N-C(CH₃)₂-C(=O)-NH-cyclohexyl] | 111° C. |

In a further example, precursors to the polymer matrix can include surface reactive additives to enhance binding with surface. Exemplary additives include functionalize acrylic monomers or functionalized acrylamide monomers. For example, an acrylic monomer can be functionalized to bind with a surface material, such as a ceramic material forming the bottom or sidewall of a well. In an example, the additive can include an acryl-phosphonate, such as methacrylphosphonate. In another example, the additive can include dimethylacrylamide or polydimethylacrylamide. In a further example, the additive can include a polylysine modified with polymerizable groups, such as acrylate groups.

In another example, polymerization can be facilitated using an atom transfer radical polymerization (ATRP). The ATRP system can include an chain transfer agent (CTA), monomer, a transition metal ion, and a ligand. An exemplary transition metal ion complex includes a copper-based complex. An exemplary ligand includes 2,2'-bipyridine, 4,4'-di-5-nonyl-2,2'-bipyridine, 4,4',4"-tris(5-nonyl)-2,2':6',2"-terpyridine, N,N,N',N',N"-pentamethyldiethylenetriamine, 1,1,4,7,10,10-hexamethyltriethylenetetramine, tris(2-dimethylaminoethyl)amine, N,N-bis(2-pyridylmethyl)octadecylamine, N,N,N',N'-tetra[(2-pyridyl)methyl]ethylenediamine, tris[(2-pyridyl)methyl]amine, tris(2-aminoethyl)amine, tris(2-bis(3-butoxy-3-oxopropyl)aminoethyl)amine, tris(2-bis(3-(2-ethylhexoxy)-3-oxopropyl)aminoethyl)amine, tris(2-bis(3-dodecoxy-3-oxopropyl)aminoethyl)amine, aliphatic, aromatic and heterocyclic/heteroaromatic amines, variations and derivatives thereof, or combinations thereof. An exemplary CTA includes 2-bromopropanitrile, ethyl 2-bromoisobutyrate, ethyl 2-bromopropionate, methyl 2-bromopropionate, 1-phenyl ethylbromide, tosyl chloride, 1-cyano-1-methylethyldiethyldithiocarbamate, 2-(N,N-diethyldithiocarbamyl)-isobutyric acid ethyl ester, dimethyl 2,6-dibromoheptanedioate, and other functionalized alkyl halides, variations or derivatives thereof, or any combination thereof. Optionally, the BRAPA monomer can function as a branching agent in the presence of an ATRP system.

In an example, ATRP is initiated at a surface to directly bond the polymer to the surface. For example, acrylate monomers, acrylamide monomers, Acrydite™ monomers, succinimidyl acrylates, bis-acrylate or bis-acrylamide monomers, derivatives thereof, or combinations thereof can be applied in solution to the initiated surface in the presence of a transition metal ion/ligand complex.

In another, the ATRP system can be used to attach a polymer to a surface of the well using a modified phosphonate, sulfonate, silicate, titanate, or zirconate compounds. In particular, an amine or hydroxyl terminated alkyl phosphonate or an alkoxy derivative thereof can be applied to a surface and initiated using an initiator. The catalyst complex and monomers can be applied, extending the surface compound.

In an exemplary method, an aqueous solution including precursors to the polymer matrix can be applied into wells of the structure defining an array of wells. The aqueous solution in the wells can be isolated by providing an immiscible fluid over the wells and initiating polymerization of the polymer precursors within the solution within the wells.

Figure 6:
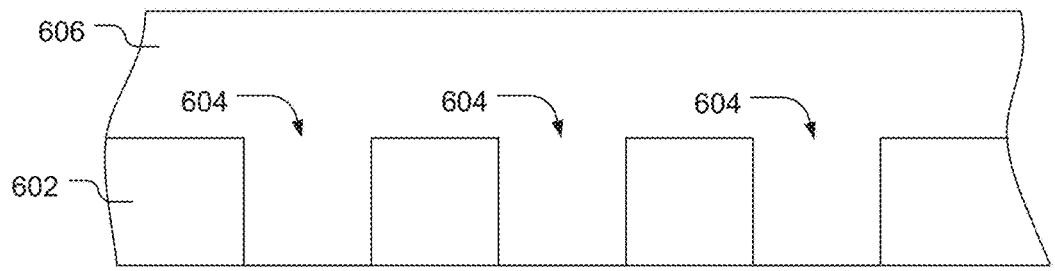
FIG. 6, FIG. 7, FIG. 8, and FIG. 9 include illustrations of workpieces during processing by an exemplary method.

For example, FIG. 6 illustrates an exemplary well structure 602 defining wells 604. One or more sensors (not illustrated) can be operatively coupled or linked to the wells 604. For example, one or more sensors can include gate structures in electrical communication to at least the bottom surface of the wells 604. An aqueous solution 606 that includes polymer precursors, among other components, is provided over the wells, distributing the solution including the polymer precursors into the wells 604. Exemplary polymer precursors include monomers, crosslinkers, initiators, or surface reactive agents, among others, such as described above. Optionally, the wells 604 can be wet prior to deposition using a hydrophilic solution, such as a solution including water, alcohol, or mixtures thereof, or a solution including water and a surfactant. An exemplary alcohol includes isopropyl alcohol. In another example, the alcohol includes ethanol. While not illustrated, the bottom surface of the well and optionally the sidewall of the well can include an ion sensitive material. Such ion sensitive material can overlie a conductive structure of an underlying electronic device, such as field effect transistor. One or more surfaces of the well can be treated with a surface reactive additive prior to applying a solution including polymer precursors.

Distributing the aqueous solutions including polymer precursors into the well 604 can be further enhanced by agitating the structure such as through spinning or vortexing. In another example, vibration, such as sonic or supersonic vibrations, can be used to improve distribution of the aqueous solution within the wells 604. In a further example, the wells can be degassed using a vacuum and the solutions applied while under a negative gauge pressure. In an example, the aqueous solution is distributed to wells at room temperature. In another example, the aqueous solution is distributed at a temperature below room temperature, particularly when an aqueous-based initiator is used. Alternatively, the aqueous solution is distributed at an elevated temperature.

Figure 7:
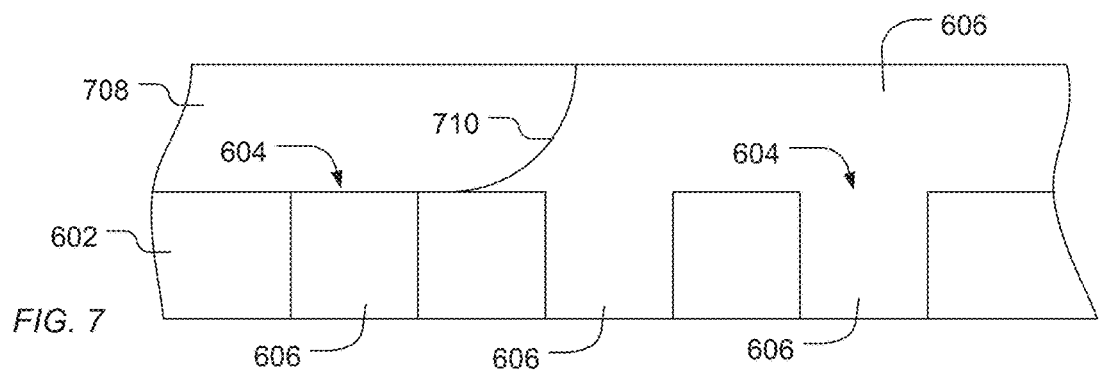
Figure 8:
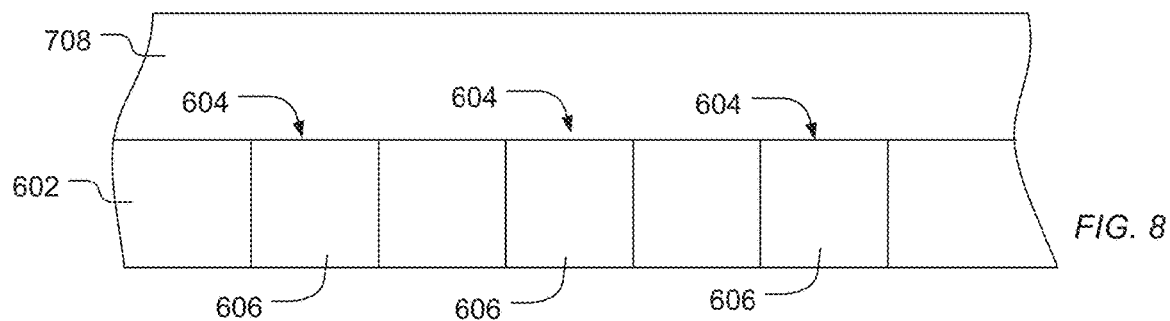

As illustrated in FIG. 7, an immiscible fluid 708 is applied over the wells 604 pushing the aqueous solution 606 away from the top of the wells and isolating the aqueous solution 606 within the wells 604, as illustrated in FIG. 8. An exemplary immiscible fluid includes mineral oil, silicone oil (e.g., poly(dimethylsiloxane)), heptane, carbonate oils (e.g. diethylhexyl carbonate (Tegosoft DEC®), or combinations thereof.

Initiators can be applied within the aqueous solution 606. Alternatively, initiators can be provided within the immiscible fluid 708. Polymerization can be initiated by changing the temperature of the substrate. Alternatively, polymerization can occur at room temperature. In particular, the polymer precursor solution can be held at a temperature in a range of 20° C. to 100° C., such as a range of 25° C. to 90° C., a range of 25° C. to 50° C., or a range of 25° C. to 45° C., for a period of time in a range of 10 minutes to 5 hours, such as a range of 10 minutes to 2 hours, or a range of 10 minutes to 1 hour.

Figure 9:
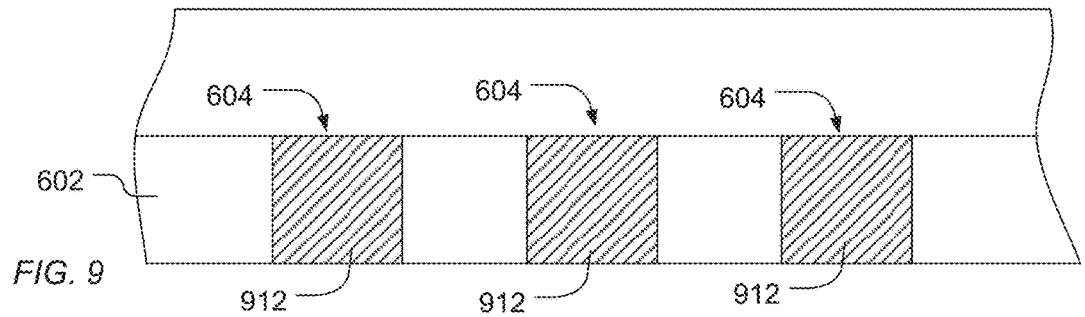

As a result of the polymerization, an array of polymer matrices 912 are formed within the wells 604 defined by the well structure 602, as illustrated in FIG. 9. Optionally, the array can be washed with a base, such as NaOH (e.g., 1 N NaOH), to remove polymer from interstitial areas between wells.

Figure 10:
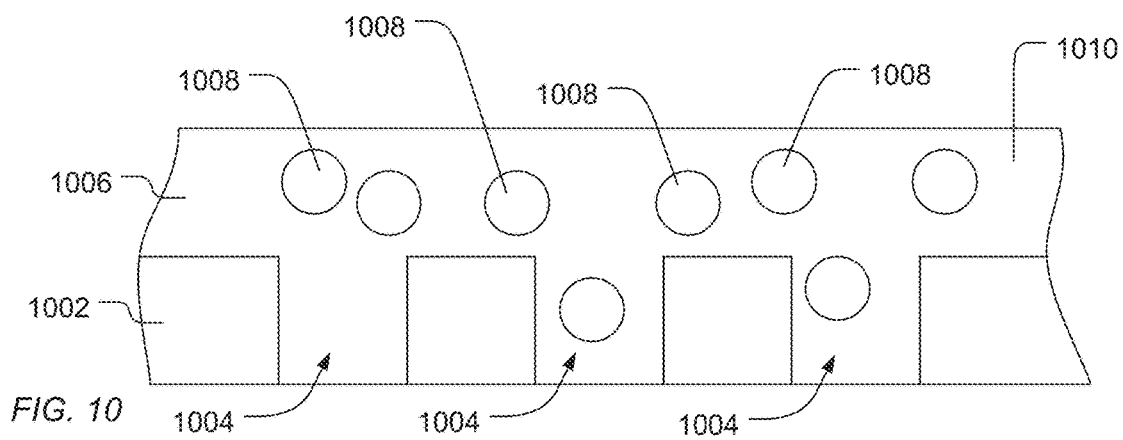
FIG. 10, FIG. 11, and FIG. 12 include illustrations of workpieces during processing by an exemplary method.

In an alternative example, an emulsion including an aqueous solution of polymer precursors as a dispersed phase within an immiscible fluid can be used to deposit droplets of aqueous solution within wells. For example, as illustrated in FIG. 10, a well structure 1002 defines wells 1004. The wells 1004 can be operatively coupled or electrically linked to one or more sensors (not illustrated). As described above, the bottom surface and optionally side surfaces of the walls of the wells 1004 can be defined by ion sensitive material layers which can overlie conductive features of underlying electronic devices.

An emulsion 1006 can include a continuous immiscible fluid 1010 and a dispersed aqueous droplets 1008 that include polymer precursors. The droplets 1008 can settle into the wells 1004. In particular, the aqueous droplets 1008 have a density greater than the immiscible fluid 1010. An exemplary immiscible fluid includes mineral oil, silicone oil (e.g., poly(dimethylsiloxane)) heptanes, carbonate oils (e.g. diethylhexyl carbonate (Tegosoft DEC®), or combinations thereof. In a further example, distribution of the aqueous droplets into wells 1004 can be facilitated by spinning, vortexing, or sonicating the fluid or structures. Optionally, the wells 1004 can be wet prior to deposition using a hydrophilic solution, such as a solution including water, alcohol, or mixtures thereof, or a solution including water and a surfactant. The temperature during distribution of the droplets into wells can be room temperature. Alternatively, the distribution can be performed at an elevated temperature.

Figure 11:
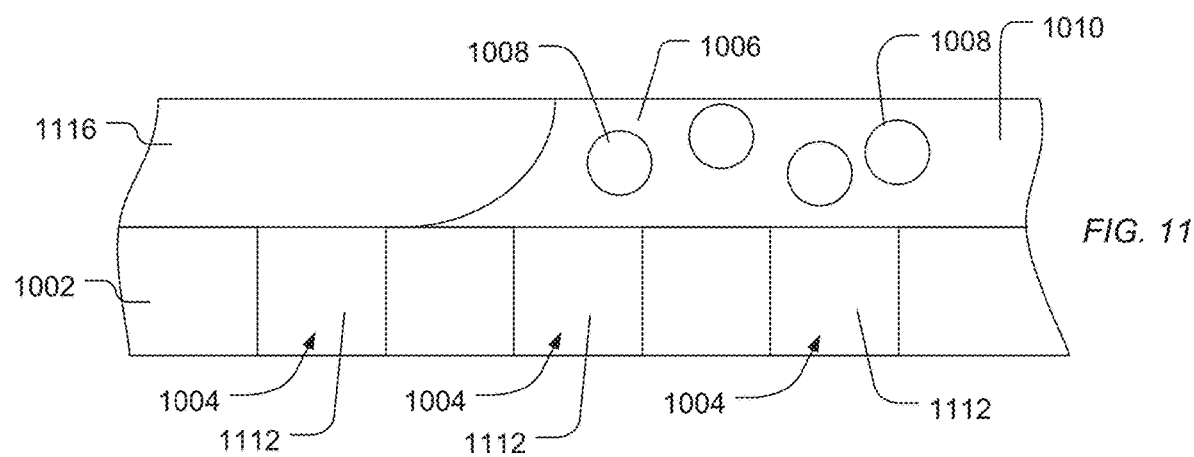
Figure 12:
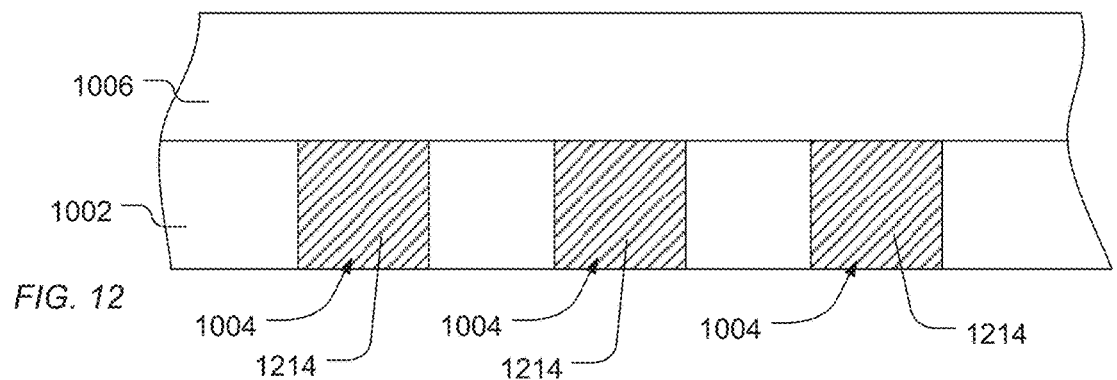

As illustrated in FIG. 11, the droplets coalesce within the wells 1004 to provide isolated solutions including polymer precursors 1112. Optionally, the emulsion 1006 can be replaced with an immiscible fluid, such as the immiscible fluid 1010 without droplets 1008 or a different immiscible fluid 1116. An exemplary immiscible fluid includes mineral oil, silicone oil (e.g., poly(dimethylsiloxane)) heptanes, carbonate oils (e.g. diethylhexyl carbonate (Tegosoft DEC®), or combinations thereof. Alternatively, the emulsion 1006 can remain in place during polymerization. As such, the solutions 1112 within the wells 1004 are isolated from the solution in other wells 1004. Polymerization can be initiated resulting in a polymer matrix 1214 within the wells 1004, as illustrated at FIG. 12. As above, polymerization can be initiated thermally. In another example, polymerization can be initiated using an oil phase initiator. Alternatively, polymerization can be initiated using an aqueous phase initiator. In particular, a second emulsion can be applied over the wells 1004. The second emulsion can include a dispersed aqueous phase including aqueous phase initiator.

Polymerization can be initiated by changing the temperature of the substrate. Alternatively, polymerization can occur at room temperature. In particular, the polymer precursor solution can be held at a temperature in a range of 20° C. to 100° C., such as a range of 25° C. to 90° C., a range of 25° C. to 50° C., or a range of 25° C. to 45° C., for a period of time in a range of 10 minutes to 5 hours, such as a range of 10 minutes to 2 hours, or a range of 10 minutes to 1 hour. Optionally, the array can be washed with a base, such as NaOH (e.g., 1 N NaOH), to remove polymer from interstitial areas between wells.

Figure 13:
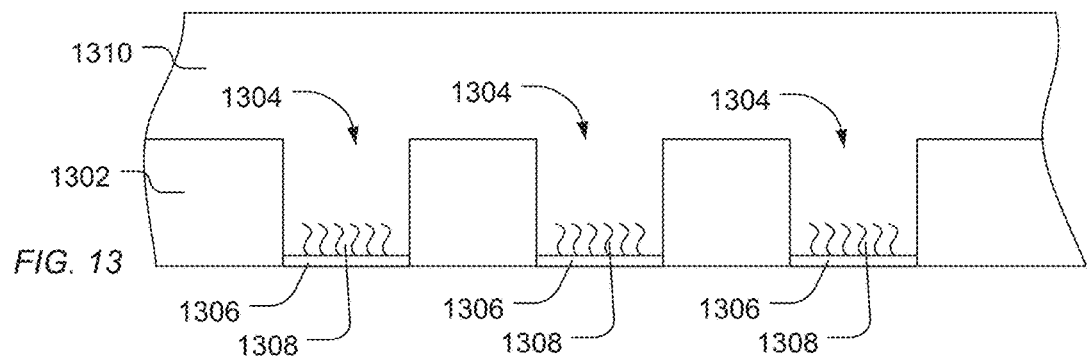
FIG. 13, FIG. 14, and FIG. 15 include illustrations of workpieces during processing by an exemplary method.

In another example, an array of matrix material can be formed within wells of a well array using initiators secured to the surface of the well array. For example, as illustrated in FIG. 13, a structure 1302 can define wells 1304. A material layer 1306 can define a lower surface of the wells 1304. Anchoring compounds 1308, such as anchoring compounds useful in Atom Transfer Radical Polymerization (ATRP), can be secured to the material layer 1306 defining a bottom surface of the wells 1304. Alternatively, a sidewall material defined within the wells or layers of the structure 1302 expose within the wells 1304 can anchor compounds such as compounds useful in ATRP, as described above.

In such an example, a solution 1310 including polymer precursors such as monomers, crosslinkers, and optionally surface reactive additive, can be applied over the structure 1302 and within the wells 1304. The anchoring compounds 1308 can be initiated to facilitate polymerization extending from the anchoring compound, isolating the polymerization within the wells 1304 and securing the polymer to the well 1304. In an example, the anchoring compound has a surface reactive group and a distal radical-forming group. The surface reactive group can include a phosphonate, a silicate, a sulfonate, a zirconate, titanate or a combination thereof. The distal radical-forming group can include an amine or hydroxyl that can undergo transfer, for example, with a halogenated (e.g., bromilated) compound and subsequently form a free-radical for use in polymerizing the polymer precursors and anchoring the resulting polymer to a well surface. In another example, the anchoring compound 1308 can include an alkyl bromoacetate modified with a surface reactive group. For example, the anchoring compound 1308 can include an alkylphosphono bromoacetate compound. The alkyl group can include between 3 and 16 carbons, such as between 6 and 16 carbons, or between 9 and 13 carbons. The alkyl group can be linear or branched. In particular, the alkyl group is linear. In a further example, the bromoacetyl group can be modified to include an alkyl modified bromoacetyl group, such as an ethyl or methyl modified bromoacetyl group forming an ester with a surface functional alkyl group. In a particular example, the anchoring compound includes the following compound:

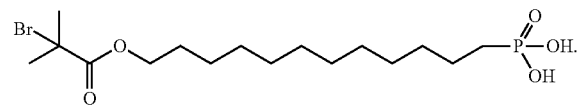 [SMILES: CC(C)(Br)C(=O)OCCCCCCCCCCCCP(=O)(O)O]

An ATRP system can be selected to terminate polymerization after a statistical average length or number of monomer additions. In such a manner, the amount polymerization within a well 1304 can be controlled. In a further example, other agents influencing chain extension or termination can be applied and added to the aqueous solution 1310.

In an alternative example, an anchoring compound, such as described above, can be included in the polymer precursor solution, such as described in relation to FIG. 6 or FIG. 10. Following curing the anchoring compound can assist with bonding a polymer to the inner surfaces of a well.

Figure 14:
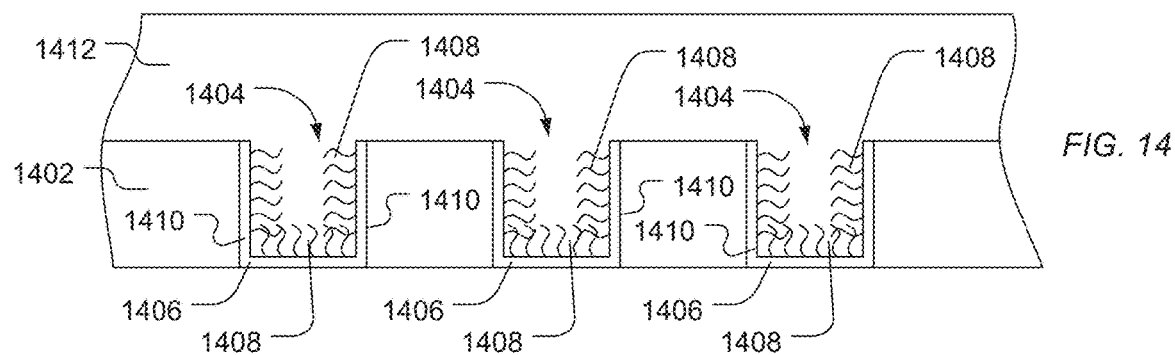

In another example illustrated in FIG. 14, a structure 1402 can define wells 1404. The wells 1404 can include a material layer 1406 that extends along sidewalls 1410 of the structure 1402 and wells 1404. The initiator 1408 can be secured to the material layer 1406 along the bottom of the well 1404 and along the sidewalls 1410. A solution 1412 including polymer precursors, crosslinkers, and other agents can be applied over the structure 1402 and the wells 1404.

Figure 15:
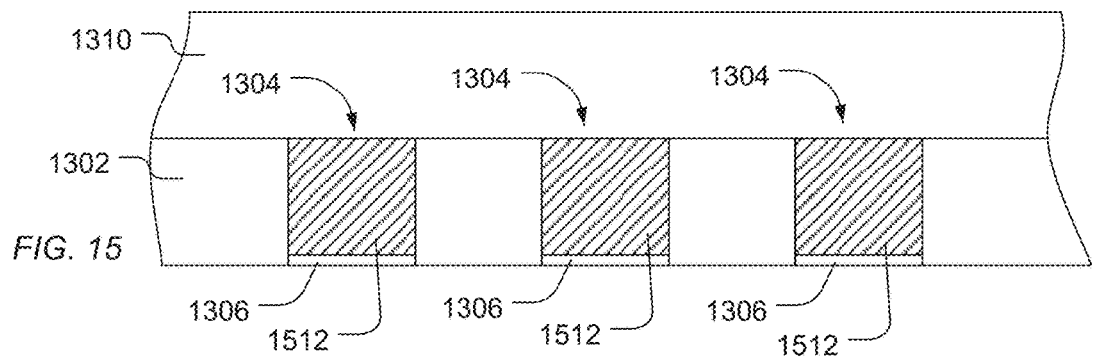

As illustrated in FIG. 15, polymer matrices 1512 are formed as a result of the initiated polymerization extending from surfaces within the wells 1304, such as surfaces defined by the material layer 1306.

Polymerization can be initiated by changing the temperature of the substrate. Alternatively, polymerization can occur at room temperature. In particular, the polymer precursor solution can be held at a temperature in a range of 20° C. to 100° C., such as a range of 25° C. to 90° C., a range of 25° C. to 50° C., or a range of 25° C. to 45° C., for a period of time in a range of 10 minutes to 5 hours, such as a range of 10 minutes to 2 hours, or a range of 10 minutes to 1 hour.

Once formed, the polymer matrices can be activated to facilitate conjugation with a target analyte, such as a polynucleotide. For example, functional groups on the polymer matrices can be enhanced to permit binding with target analytes or analyte receptors (e.g., oligonucleotide primers). In a particular example, functional groups of the hydrophilic polymer matrix can be modified with reagents capable of converting the hydrophilic polymer functional groups to reactive moieties that can undergo nucleophilic or electrophilic substitution. For example, hydroxyl groups on the polymer matrices can be activated by replacing at least a portion of the hydroxyl groups with a sulfonate group or chlorine. Exemplary sulfonate groups can be derived from tresyl, mesyl, tosyl, or fosyl chloride, or any combination thereof. Sulfonate can act to permit nucleophiles to replace the sulfonate. The sulfonate can further react with liberated chlorine to provide chlorinated functional groups that can be used in a process to conjugate the matrix. In another example, amine groups on the polymer matrices can be activated.

For example, target analyte or analyte receptors can bind to the hydrophilic polymer through nucleophilic substitution with the sulfonate group. In particular example, target analyte receptors terminated with a nucleophile, such as an amine or a thiol, can undergo nucleophilic substitution to replace the sulfonate groups in the polymer matrices. As a result of the activation, conjugated polymer matrices can be formed.

In another example, the sulfonated polymer matrices can be further reacted with mono- or multi-functional mono- or multi-nucleophilic reagents that can form an attachment to the matrix while maintaining nucleophilic activity for oligonucleotides comprising electrophilic groups, such as maleimide. In addition, the residual nucleophilic activity can be converted to electrophilic activity by attachment to reagents comprising multi-electrophilic groups, which are subsequently to attach to oligonucleotides comprising nucleophilic groups.

In another example, a monomer containing the functional group can be added during the polymerization. The monomer can include, for example, an acrylamide containing a carboxylic acid, ester, halogen or other amine reactive group. The ester group can be hydrolyzed before the reaction with an amine oligo.

Other conjugation techniques include the use of monomers that comprise amines. The amine group is a nucleophilic group that can be further modified with amine reactive bi-functional bis-electrophilic reagents that yield a mono-functional electrophilic group subsequent to attachment to the polymer matrix. Such an electrophilic group can be reacted with oligonucleotides having a nucleophilic group, such as an amine or thiol, causing attachment of the oligonucleotide by reaction with the vacant electrophile.

If the polymer matrix is prepared from a combination of amino- and hydroxyl-acrylamides, the polymer matrix includes a combination of nucleophilic amino groups and neutral hydroxyl groups. The amino groups can be modified with di-functional bis-electrophilic moieties, such as a di-isocyanate or bis-NHS ester, resulting in a hydrophilic polymer matrix reactive to nucleophiles. An exemplary bis-NHS ester includes bis-succinimidyl C2-C12 alkyl esters, such as bis-succinimidyl suberate or bis-succinimidyl glutarate.

Other activation chemistries include incorporating multiple steps to convert a specified functional group to accommodate specific desired linkages. For example, the sulfonate modified hydroxyl group can be converted into a nucleophilic group through several methods. In an example, reaction of the sulfonate with azide anion yields an azide substituted hydrophilic polymer. The azide can be used directly to conjugate to an acetylene substituted biomolecule via "CLICK" chemistry that can be performed with or without copper catalysis. Optionally, the azide can be converted to amine by, for example, catalytic reduction with hydrogen or reduction with an organic phosphine. The resulting amine can then be converted to an electrophilic group with a variety of reagents, such as di-isocyanates, bis-NHS esters, cyanuric chloride, or a combination thereof. In an example, using di-isocyanates yields a urea linkage between the polymer and a linker that results in a residual isocyanate group that is capable of reacting with an amino substituted biomolecule to yield a urea linkage between the linker and the biomolecule. In another example, using bis-NHS esters yields an amide linkage between the polymer and the linker and a residual NHS ester group that is capable of reacting with an amino substituted biomolecule to yield an amide linkage between the linker and the biomolecule. In a further example, using cyanuric chloride yields an amino-triazine linkage between the polymer and the linker and two residual chloro-triazine groups one of which is capable of reacting with an amino substituted biomolecule to yield an amino-triazine linkage between the linker and the biomolecule. Other nucleophilic groups can be incorporated into the matrix via sulfonate activation. For example, reaction of sulfonated matrices with thiobenzoic acid anion and hydrolysis of the consequent thiobenzoate incorporates a thiol into the matrix which can be subsequently reacted with a maleimide substituted biomolecule to yield a thio-succinimide linkage to the biomolecule.

Thiol can also be reacted with a bromo-acetyl group or bromo-amidyl group. In a particular example, when n-(5-bromoacetamidylpentyl)acrylamide (BRAPA) is included as a comonomer, oligonucleotides can be incorporated by forming a thiobenzamide-oligonucleotide compound, for example, as illustrated below, for reacting with bromo-acetyl groups on the polymer.

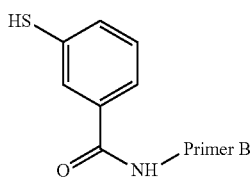

The thiobenzamide-oligonucleotide compound can be formed by reacting the following dithiobenzoate-NHS compound with an amine terminated oligonucleotide and activating the dithiobenzamide-oligonucleotide compound to form the above illustrated thiobenzamide-oligonucleotide compound.

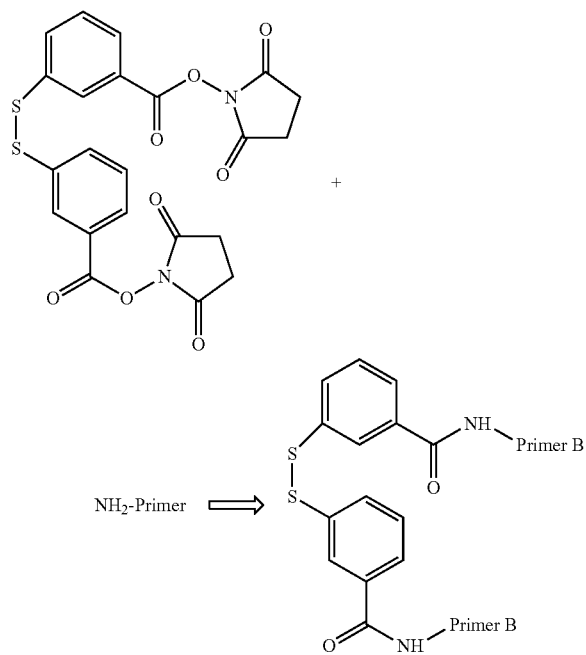

Alternatively, acrydite oligonucleotides can be used during the polymerization to incorporate oligonucleotides. An exemplary acrydite oligonucleotide can include an ion-exchanged oligonucleotide.

Covalent linkages of biomolecules onto refractory or polymeric substrates can be created using electrophilic moieties on the substrate coupled with nucleophilic moieties on the biomolecule or nucleophilic linkages on the substrate coupled with electrophilic linkages on the biomolecule. Because of the hydrophilic nature of most common biomolecules of interest, the solvent of choice for these couplings is water or water containing some water soluble organic solvent in order to disperse the biomolecule onto the substrate. In particular, polynucleotides are generally coupled to substrates in water systems because of their poly-anionic nature. Because water competes with the nucleophile for the electrophile by hydrolyzing the electrophile to an inactive moiety for conjugation, aqueous systems can result in low yields of coupled product, where the yield is based on the electrophilic portion of the couple. When high yields of electrophilic portion of the reaction couple are desired, high concentrations of the nucleophile drive the reaction and mitigate hydrolysis, resulting in inefficient use of the nucleophile. In the case of polynucleic acids, the metal counter ion of the phosphate can be replaced with a lipophilic counter-ion, in order to help solubilize the biomolecule in polar, non-reactive, non-aqueous solvents. These solvents can include amides or ureas such as formamide, N,N-dimethylformamide, acetamide, N,N-dimethylacetamide, hexamethylphosphoramide, pyrrolidone, N-methylpyrrolidone, N,N,N',N'-tetramethylurea, N,N'-dimethyl-N,N'-trimethyleneurea, or a combination thereof; carbonates such as dimethyl carbonate, propylene carbonate, or a combination thereof; ethers such as tetrahydrofuran; sulfoxides and sulfones such as dimethylsulfoxide, dimethylsulfone, or a combination thereof, hindered alcohols such as tert-butyl alcohol; or a combination thereof. Lipophilic cations can include tetraalkylammomiun or tetraarylammonium cations such as tetramethylamonium, tetraethylamonium, tetrapropylamonium, tetrabutylamonium, tetrapentylamonium, tetrahexylamonium, tetraheptylamonium, tetraoctylamonium, and alkyl and aryl mixtures thereof, tetraarylphosphonium cations such as tetraphenylphosphonium, tetraalkylarsonium or tetraarylarsonium such as tetraphenylarsonium, and trialkylsulfonium cations such as trimethylsulfonium, or a combination thereof. The conversion of polynucleic acids into organic solvent soluble materials by exchanging metal cations with lipophilic cations can be performed by a variety of standard cation exchange techniques.

In a particular embodiment, the polymer matrices are exposed to target polynucleotides having a segment complementary to oligonucleotides conjugated to the polymer matrices. The polynucleotides are subjected to amplification, such as through polymerase chain reaction (PCR) or recombinase polymerase amplification (RPA). For example, the target polynucleotides are provided in low concentrations such that a single polynucleotide is likely to reside within a single polymer matrix of the array of polymer matrices. The polymer matrix can be exposed to enzymes, nucleotides, salts or other components sufficient to facilitate duplication of the target polynucleotide.

In a particular embodiment, an enzyme such as a polymerase is present, bound to, or is in close proximity to the polymer matrix. A variety of nucleic acid polymerase can be used in the methods described herein. In an exemplary embodiment, the polymerase can include an enzyme, fragment or subunit thereof, which can catalyze duplication of the polynucleotide. In another embodiment, the polymerase can be a naturally-occurring polymerase, recombinant polymerase, mutant polymerase, variant polymerase, fusion or otherwise engineered polymerase, chemically modified polymerase, synthetic molecules, or analog, derivative or fragment thereof.

In an embodiment, the polymerase can be any Family A DNA polymerase (also known as pol I family) or any Family B DNA polymerase. In embodiments, the DNA polymerase can be a recombinant form capable of duplicating polynucleotides with superior accuracy and yield as compared to a non-recombinant DNA polymerase. For example, the polymerase can include a high-fidelity polymerase or thermostable polymerase. In embodiments, conditions for duplication of polynucleotides can include 'Hot Start' conditions, for example Hot Start polymerases, such as Amplitaq Gold® DNA polymerase (Applied Biosciences) or KOD Hot Start DNA polymerase (EMD Biosciences). Typically, a 'Hot Start' polymerase includes a thermostable polymerase and one or more antibodies that inhibit the DNA polymerase and 3'-5' exonuclease activities at ambient temperature.

In embodiments, the polymerase can be an enzyme such as Taq polymerase (from *Thermus aquaticus*), Tfi polymerase (from *Thermus filiformis*), Bst polymerase (from

*Bacillus stearothermophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*).

In embodiments, the polymerase can be a recombinant form of *Thermococcus kodakaraensis*. In embodiments, the polymerase can be a KOD or KOD-like DNA polymerase such as KOD polymerase (EMD Biosciences), KOD "Hot Start" polymerase (EMD Biosciences), KOD Xtreme Hot Start DNA Polymerase (EMD Biosciences), KOD XL DNA polymerase (EMD Biosciences), Platinum® Taq DNA Polymerase (Invitrogen), Platinum® Taq DNA Polymerase High Fidelity (Invitrogen), Platinum® Pfx (Invitrogen), Accuprime™ Pfx (Invitrogen), Accuprime™ Taq DNA Polymerase High Fidelity (Invitrogen) or Amplitaq Gold® DNA Polymerase (Applied Biosystems). In embodiments, the polymerase can be a DNA polymerase containing analogous mutations to those polymerases discussed herein.

In particular, the polynucleotide to be amplified can be captured by the polymer matrix. Exemplary methods for capturing nucleic acid can include: hybridizing a polynucleotide to an oligonucleotide that is attached to a polymer matrix. In embodiments, methods for capturing nucleic acids comprise: (a) providing a polymer matrix attached to a single-stranded oligonucleotide (e.g., a capture oligonucleotide); (b) providing a single-stranded polynucleotide; and (c) hybridizing the single-stranded oligonucleotide to the single-stranded polynucleotides, thereby capturing the single-stranded polynucleotide to the polymer matrix. Each of the polymer matrices can be attached with a plurality of single-stranded oligonucleotides (e.g., capture oligonucleotides). Step (c) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide.

In an example, the method further includes amplifying the polynucleotide into a plurality of polynucleotides and attaching at least a portion of the plurality of polynucleotides to the polymer matrix, thereby generating a polymer matrix including a plurality of attached polynucleotides. Alternatively, the method can further include amplifying the polynucleotide into a plurality of complementary polynucleotides by extending the oligonucleotide, thereby generating a polymer matrix including a plurality of attached polynucleotides.

In embodiments, methods for nucleotide incorporation comprise: conducting a nucleotide polymerization reaction on a polynucleotide that is hybridized to an oligonucleotide that is attached to a polymer matrix. In embodiments, methods for nucleotide incorporation comprise: (a) providing a polymer matrix attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby conducting nucleotide incorporation. In embodiments, each of the polymer matrices can be attached with a plurality of single-stranded oligonucleotides (e.g., capture oligonucleotides). Steps (b), (c) or (d) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, a system comprises a single-stranded polynucleotide hybridized to a single-stranded oligonucleotide which is attached to a polymer matrix, wherein at least one nucleotide is polymerized onto the end of the single-stranded oligonucleotide.

In embodiments, methods for primer extension comprise: conducting a primer extension reaction on a polynucleotide that is hybridized to an oligonucleotide that is attached to a polymer matrix. In embodiments, methods for nucleic acid primer extension comprise: (a) providing a polymer matrix attached to a single-stranded oligonucleotide (e.g., a primer oligonucleotide); (b) providing a single-stranded template polynucleotide; (c) hybridizing the single-stranded oligonucleotide to the single-stranded template polynucleotide; and (d) contacting the single-stranded template polynucleotide with a polymerase and at least one nucleotide under conditions suitable for the polymerase to catalyze polymerization of at least one nucleotide onto the single-stranded oligonucleotide, thereby extending the primer. In embodiments, each of the polymer matrices can be attached with a plurality of single-stranded oligonucleotides (e.g., capture oligonucleotides). In embodiments, step (b), (c) or (d) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, a system comprises a single-stranded polynucleotide hybridized to a single-stranded oligonucleotide which is attached to a polymer matrix, wherein the single-stranded oligonucleotide is extended with one or more nucleotides.

In embodiments, methods for nucleic acid amplification comprise: conducting a primer extension reaction on a polynucleotide that is hybridized to an oligonucleotide which is attached to a polymer matrix. In embodiments, methods for nucleic acid amplification comprise: (a) providing a polymer matrix attached to a single-stranded oligonucleotide (e.g., a primer oligonucleotide); (b) providing a single-stranded template polynucleotide; (c) hybridizing the single-stranded oligonucleotide to the single-stranded template polynucleotide; (d) contacting the single-stranded template polynucleotide with a polymerase and at least one nucleotide under conditions suitable for the polymerase to catalyze polymerization of at least one nucleotide onto the single-stranded oligonucleotide so as to generate an extended single-stranded oligonucleotide. In embodiments, the method further comprises: (e) removing (e.g., denaturing) the single-stranded template polynucleotide from the extended single-stranded oligonucleotide so that the single-stranded oligonucleotide remains attached to the polymer matrix; (f) hybridizing the remaining single-stranded oligonucleotide to a second single-stranded template polynucleotide; and (g) contacting the second single-stranded template polynucleotide with a second polymerase and a second at least one nucleotide, under conditions suitable for the second polymerase to catalyze polymerization of the second at least one nucleotide onto the single-stranded oligonucleotide so as to generate a subsequent extended single-stranded oligonucleotide. In embodiments, steps (e), (f) and (g) can be repeated at least once. In embodiments, the polymerase and the second polymerase comprise a thermostable polymerase. In embodiments, the conditions suitable for nucleotide polymerization include conducting the nucleotide polymerization steps (e.g., steps (d) or (g)) at an elevated temperature. In embodiments, the conditions suitable for nucleotide polymerization include conducting the nucleotide polymerization step (e.g., steps (d) or (g)) at alternating temperatures (e.g., an elevated temperature and a relatively lower temperature). In embodiments, the alternating temperature ranges from 60-95° C. In embodiments, the temperature cycles can be about 10 seconds to about 5 minutes, or about 10 minutes, or about 15 minutes, or longer. In embodiments, methods for nucleic acid amplification can generate one or more polymer matrices each attached to a plurality of template polynucleotides comprising sequences that are complementary to the single-stranded template polynucleotide or to the second single-stranded template polynucleotide. In embodiments, each of the polymer matrices can be attached with a plurality of single-stranded oligonucleotides (e.g., capture oligonucleotides). In embodiments, step (b), (c), (d), (e), (f) or (g) can be conducted with a plurality of single-stranded polynucleotides. In embodiments, at least a portion of the single-stranded oligonucleotide comprises a nucleotide sequence that is complementary (or partially complementary) to at least a portion of the single-stranded polynucleotide. In embodiments, methods for nucleic acid amplification (as described above) can be conducted in an aqueous phase solution in an oil phase (e.g., dispersed phase droplet).

Following PCR or RPA, amplified polymer matrices are formed. Polymer matrices of the array of polymer matrices can be monoclonal, including a copies of a single species of target polynucleotide. The polynucleotides can extend within the polymer matrix. Hydrogel and hydrophilic polymer matrices having a low concentration of polymer relative to water can include polynucleotide segments on the interior of and throughout the polymer matrix. In particular, the polymer matrix can permit diffusion of enzymes, nucleotides, primers and reaction products used to monitor the reaction. A high number of polynucleotides per matrix produces a better signal.

In an example, a polymer matrix in water can be not greater than 50 wt % polymer, such as not greater than 30 wt % polymer, not greater than 20 wt % polymer, not greater than 10 wt % polymer, not greater than 5 wt % polymer, or even not greater than 2 wt % polymer. In an example, the polymer matrix can include at least 0.01 wt. % polymer.

In an additional example, the polymer matrix can have a porosity permitting diffusion of proteins and enzymes. In an example, the polymer matrix can have a porosity to permit diffusion of proteins having a size of at least 50 kilodaltons, such as at least 100 kilodaltons, at least 200 kilodaltons, at least 250 kilodaltons, or even at least 350 kilodaltons. In an example, proteins having a size of 10 kilodaltons are restricted.

In another example, when conjugated, the polymer matrix can include a density of polynucleotides, termed nucleotide density, of at least $7 \times 10^4$ per $\mu m^3$. For example, the nucleotide density can be at least $10^5$ per $\mu m^3$, such as at least $10^6$ per $m^3$, at least $5 \times 10^6$ per $\mu m^3$, at least $8 \times 10^6$ per $m^3$, at least $1 \times 10^7$ per $\mu m^3$, or even at least $3 \times 10^7$ per $\mu m^3$. In a further example, the nucleotide density can be not greater than $10^{15}$ per $\mu m^3$.

In an exemplary embodiment, the polymer matrix array can be utilized in a sequencing device. For example, a sequencing device can include the array of wells within which the polymer matrices are formed. Enzymes and nucleotides can be provided to the wells to facilitate detectible reactions, such as nucleotide incorporation.

Sequencing can be performed by detecting nucleotide addition. Nucleotide addition can be detected using methods such as fluorescent emission methods or ion detection methods. For example, a set of fluorescently labeled nucleotides can be provided to the system and can migrate to the well. Excitation energy can be also provided to the well. When a nucleotide is captured by a polymerase and added to the end of an extending primer, a label of the nucleotide can fluoresce, indicating which type of nucleotide is added.

In an alternative example, solutions including a single type of nucleotide can be fed sequentially. In response to nucleotide addition, the pH within the local environment of the well can change. Such a change in pH can be detected by ion sensitive field effect transistors (ISFET). As such, a change in pH can be used to generate a signal indicating the order of nucleotides complementary to the polynucleotide of the polymer matrix.

In particular, a sequencing system can include a well, or a plurality of wells, disposed over a sensor pad of an ionic sensor, such as a field effect transistor (FET). In embodiments, a system includes a polymer matrix in a well which is disposed over a sensor pad of an ionic sensor (e.g., FET), or a polymer matrix in a plurality of wells which are disposed over sensor pads of ionic sensors (e.g., FET). In embodiments, an FET can be a chemFET or an ISFET. A "chemFET" or chemical field-effect transistor, includes a type of field effect transistor that acts as a chemical sensor. The chemFET has the structural analog of a MOSFET transistor, where the charge on the gate electrode is applied by a chemical process. An "ISFET" or ion-sensitive field-effect transistor, can be used for measuring ion concentrations in solution; when the ion concentration (such as H+) changes, the current through the transistor changes accordingly.

In embodiments, the FET can be a FET array. As used herein, an "array" is a planar arrangement of elements such as sensors or wells. The array can be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs. In an example, the FET array can include not more than $10^{15}$ FETs.

In embodiments, one or more microfluidic structures can be fabricated above the FET sensor array to provide for containment or confinement of a biological or chemical reaction. For example, in one implementation, the microfluidic structure(s) can be configured as one or more wells (or microwells, or reaction chambers, or reaction wells, as the terms are used interchangeably herein) disposed above one or more sensors of the array, such that the one or more sensors over which a given well is disposed detect and measure analyte presence, level, or concentration in the given well. In embodiments, there can be a 1:1 correspondence of FET sensors and reaction wells.

In another example, a well of the array of wells can be operatively connected to measuring devices. For example, for fluorescent emission methods, a well can be operatively coupled to a light detection device. In the case of ionic detection, the lower surface of the well can be disposed over a sensor pad of an ionic sensor, such as a field effect transistor.

One exemplary system involving sequencing via detection of ionic byproducts of nucleotide incorporation is the Ion Torrent PGM™ or Proton™ sequencer (Life Technologies), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion Torrent PGM™ or Proton™ sequencer detects the nucleotide incorporations by detecting the hydrogen ion byproducts of the nucleotide incorporations. The Ion Torrent PGM™ or Proton™ sequencer can include a plurality of template polynucleotides to be sequenced, each template disposed within a respective sequencing reaction well in an array. The wells of the array can each be coupled to at least one ion sensor that can detect the release of H+ ions or changes in solution pH produced as a byproduct of nucleotide incorporation. The ion sensor comprises a field effect transistor (FET) coupled to an ion-sensitive detection layer that can sense the presence of H+ ions or changes in solution pH resulting from nucleotide incorporation. The ion sensor can provide output signals indicative of nucleotide incorporation which can be represented as voltage changes whose magnitude correlates with the H+ ion concentration in a respective well or reaction chamber. Different nucleotide types can be flowed serially into the reaction chamber, and can be incorporated by the polymerase into an extending primer (or polymerization site) in an order determined by the sequence of the template. Each nucleotide incorporation can be accompanied by the release of H+ ions in the reaction well, along with a concomitant change in the localized pH. The release of H+ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion Torrent PGM™ or Proton™ sequencers can be found, for example, in U.S. patent application Ser. No. 12/002,781, now published as U.S. Patent Publication No. 2009/0026082 and issued U.S. Pat. No. 8,262,900; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

EXAMPLE

An ION Proton Chip is pretreated with 165 microliters of 1 N NaOH solution for 3 minutes and washed twice with 1 mL of deionized water and twice with methanol. Remaining methanol is removed by suction. The chip is dried under vacuum in a desiccator for 20 minutes.

In a 15 mL tube, a polymer mixture is prepared by mixing 160 mg of acrylamide and 5 mL water. The solution is sparged with $N_2$ for 20 minutes. To the solution, 165 mg of a 10% wt/v solution of n-(5-bromoacetamidylpentyl)acrylamide (BRAPA) is added. In addition, 11.5 mg of 11.5 mg of tetramethylethylenediamine (TMEDA) and 100 microliters of a 5% wt/v solution of ammonium persulfate (APS) are added. The solution is vortexed briefly.

The chip is further treated by adding 165 microliters of the polymer mixture though the entry port until the exit reservoir is covered. The entry reservoir is covered with the remainder of the polymer mixture. Both reservoirs are covered with tape. The chip is incubated for 90 min at room temperature. Optionally the chip can be centrifuged for 1 minute immediately after taping. After 90 min, the extra polymer solution is suctioned from the entry reservoir. The chip is washed five times with 1 mL of water over 20 minutes. Optionally, the chip is washed with 1N NaOH for a period of 1 minute to 10 minutes for 1 to 5 times. The chip is filled with water and taped.

To functionalize the chip, a solution is prepared by formulating a 1 mM solution of benzthio B primer TEA salt, in DMSO, from either a dried aliquot, or a 1 mM aqueous aliquot. If formulation is from an aqueous aliquot, an aliquot of DMSO 50% larger than the aqueous aliquot is added to the aqueous aliquot, and evaporated on Speedvac until the volume is reduced to the initial aqueous aliquot volume. (~45 min). Four equivalents of a freshly made 100 mM DTT/DMSO solution are added. (~100 ul of a 1 mM oligo solution is treated with 4 uL of the 100 mM DTT/DMSO solution.) DTT is dithiothreotol.

After 10 minutes the DTT treated oligo/DMSO solution is diluted to 200 uM with a DMSO solution that is 1000 parts DMSO/50 parts DMSO saturated with sodium iodide/50 parts diisopropylethylamine. The solution is briefly vortexed. This approach usually provides 4 volumes of diluent to 1 volume DTT/oligo DMSO solution. The solution is used immediately.

The chips are suctioned dry chips until no more surface water is observed in chip. An amount of 135 microliters of functionalization solution are added through the entry port until the exit reservoir is covered. The remainder of the solution is used to cover the entry reservoir. The entry and exit ports are covered with tape. The chip is incubated at room temp for at least one hour, generally two to three. The tape is removed, and the chip is wash four times with 1 mL of water. The chip is stored under water and the reservoirs are covered with tape.

In particular, embodiments of the above systems and methods provide technical advantages including deposition into small wells defining volumes on the order of 0.05 fL to 1 pL. Such deposition techniques are particularly advantageous for depositing polymer matrices into wells defining volumes on the order of 0.05 fL to 10 fL.

In a first aspect, a method of forming a polymer matrix array includes applying an aqueous solution into wells of a well array, the aqueous solution comprising polymer precursors, applying an immiscible fluid over the well array to isolate the aqueous solution within the wells of the well array, and polymerizing the polymer precursors isolated in the wells of the well array to form the polymer matrix array.

In an example of the first aspect, the well has a characteristic diameter in a range of 0.1 micrometers to 2 micrometers. In another example of the first aspect and the above examples, the well has a thickness in a range of 0.01 micrometers to 10 micrometers.

In a further example of the first aspect and the above examples, the wells of the well array overlie sensors of a sensor array, the wells corresponding to ion sensitive material of the sensors of the sensor array.

In an additional example of the first aspect and the above examples, a polymer matrix of the polymer matrix array is conformal with walls of a well of the well array.

In another example of the first aspect and the above examples, the polymer precursors include a radically polymerizable monomer. For example, the radically polymerizable monomer includes a vinyl-based monomer. In an example, the vinyl-based monomer includes acrylamide, vinyl acetate, hydroxyalkylmethacrylate, variations or derivatives thereof or any combination thereof.

In a further example of the first aspect and the above examples, the polymer precursors include a crosslinker. For example, the crosslinker is a bis-acrylamide.

In an additional example of the first aspect and the above examples, the polymer precursors include a surface active additive.

In another example of the first aspect and the above examples, the polymer precursors include an oligonucleotide functionalized acrylamide. In an additional example of the first aspect and the above examples, the polymer precursors include N-(5-bromoacetamidylpentyl)acrylamide.

In a further example of the first aspect and the above examples, applying the aqueous solution includes applying an emulsion including the aqueous solution as a dispersed phase.

In an additional example of the first aspect and the above examples, the immiscible fluid includes mineral oil, silicone oil, heptane, carbonate oils, or combinations thereof.

In another example of the first aspect and the above examples, the method further includes spinning the well array following applying the aqueous solution.

In a further example of the first aspect and the above examples, the method further includes sonicating the well array following applying the aqueous solution.

In an additional example of the first aspect and the above examples, the method further includes degassing the well array during applying the aqueous solution.

In another example of the first aspect and the above examples, the method further includes wetting the well array with a hydrophilic fluid prior to applying the aqueous solution.

In a further example of the first aspect and the above examples, the polymer precursors include an initiator.

In an additional example of the first aspect and the above examples, the immiscible fluid includes an initiator.

In another example of the first aspect and the above examples, the method further includes treating a surface within the well with a surface active agent prior to applying the aqueous solution.

In a second aspect, a method of forming a polymer matrix array includes applying an emulsion over wells of a well array. The emulsion includes an aqueous dispersed phase in an immiscible continuous phase. The aqueous dispersed phase includes polymer precursors. The dispersed phase coalesces in the wells of the well array. The method further includes applying a second immiscible fluid over the wells of the well array to displace the emulsion and polymerizing the polymer precursors in the wells of the well array to form the polymer matrix array.

In an example of the second aspect, the wells have a characteristic diameter in a range of 0.1 micrometers to 2 micrometers. In another example of the second aspect and the above examples, the wells have a thickness in a range of 0.01 micrometers to 10 micrometers.

In a further example of the second aspect and the above examples, the wells of the well array overlie sensors of a sensor array, the wells corresponding to ion sensitive material of the sensors of the sensor array.

In an additional example of the second aspect and the above examples, a polymer matrix of the polymer matrix array is conformal with walls of a well of the well array.

In another example of the second aspect and the above examples, the polymer precursors include a radically polymerizable monomer. For example, the radically polymerizable monomer includes a vinyl-based monomer. In an example, the vinyl-based monomer includes acrylamide, vinyl acetate, hydroxyalkylmethacrylate, variations or derivatives thereof or any combination thereof.

In a further example of the second aspect and the above examples, the polymer precursors include a crosslinker. In an example, the crosslinker is a bis-acrylamide.

In an additional example of the second aspect and the above examples, the polymer precursors include a surface active additive.

In another example of the second aspect and the above examples, the polymer precursors include an oligonucleotide functionalized acrylamide.

In a further example of the second aspect and the above examples, the polymer precursors include N-(5-bromoacetamidylpentyl)acrylamide.

In an additional example of the second aspect and the above examples, the immiscible fluid includes mineral oil, silicone oil, heptane, carbonate oils, or combinations thereof.

In another example of the second aspect and the above examples, the method further includes spinning the well array following applying the aqueous solution.

In a further example of the second aspect and the above examples, the method further includes sonicating the well array following applying the aqueous solution.

In an additional example of the second aspect and the above examples, the method further includes degassing the well array during applying the aqueous solution.

In another example of the second aspect and the above examples, the method further includes wetting the well array with a hydrophilic fluid prior to applying the aqueous solution.

In a further example of the second aspect and the above examples, the polymer precursors include an initiator.

In an additional example of the second aspect and the above examples, the immiscible fluid includes an initiator.

In another example of the second aspect and the above examples, the method further includes treating a surface within the well with a surface active agent prior to applying the aqueous solution.

In a third aspect, a method of forming a polymer matrix array includes treating a surface within a well of a well array with a surface compound including a surface reactive functional group and a radical-forming distal group, applying an aqueous solution including polymer precursors to the well of the well array, and activating the radical-forming distal group of the surface coupling compound with an initiator and atom transfer radical polymerization (ATRP) catalyst to initiate radical polymerization of the polymer precursors within the well of the well array to form the polymer matrix array.

In an example of the third aspect, the surface reactive functional group includes phosphonate.

In another example of the third aspect and the above examples, the radical-forming distal group includes an amine or a hydroxyl group.

In a further example of the third aspect and the above examples, the well has a characteristic diameter in a range of 0.1 micrometers to 2 micrometers. In an additional example of the third aspect and the above examples, the well has a thickness in a range of 0.01 micrometers to 10 micrometers.

In another example of the third aspect and the above examples, wells of the well array overlie sensors of a sensor array, the wells corresponding to ion sensitive material of the sensors of the sensor array.

In a further example of the third aspect and the above examples, the polymer precursors include a radically polymerizable monomer. For example, the radically polymerizable monomer includes a vinyl-based monomer. In an example, the vinyl-based monomer includes acrylamide, vinyl acetate, hydroxyalkylmethacrylate, variations or derivatives thereof or any combination thereof In an additional example of the third aspect and the above examples, the polymer precursors include an oligonucleotide functionalized acrylamide.

In another example of the third aspect and the above examples, the polymer precursors include N-(5-bromoacetamidylpentyl)acrylamide.

In a further example of the third aspect and the above examples, the polymer precursors include a crosslinker. For example, the crosslinker is a bis-acrylamide.

In a fourth aspect, a method includes curing a polymer matrix within a well of an array of wells. The polymer matrix is formed from precursors including an acrylate or an acrylamide and a bromine functionalized acrylate or acrylamide. The method further includes applying a thiobenzoate oligonucleotide complex to the cured polymer. The thiobenzamide oligonucleotide complex reacts with the polymer matrix to form an oligonucleotide conjugated polymer matrix.

In an example of the fourth aspect, the bromine functionalized acrylate or acrylamide include N-(5-bromoacetamidylpentyl)acrylamide.

In another example of the fourth aspect and the above examples, the acrylate or acrylamide includes hydroxyalkylacrylamide.

In a further example of the fourth aspect and the above examples, the method further includes applying a target polynucleotide under amplification conditions to the oligonucleotide conjugated polymer matrix, wherein the oligonucleotide comprises sequences complementary to a portion of the target polynucleotide. In an example, the oligonucleotide is extended based at least in part on the target polynucleotide. In an additional example, the method further includes sequencing the extended oligonucleotide using a sensor operatively coupled to the well. In another example, sequencing includes sequentially applying solutions including nucleotides to the polymer matrix and measuring a response with the sensor.

In a fifth aspect, an apparatus includes a sensor array including a plurality of sensors, each sensor including an ion sensitive material layer. The apparatus further includes a well array disposed over the sensor array and defining wells corresponding to sensors of the plurality of sensors. The ion sensitive material layer of a sensor forms a bottom surface of a corresponding well. The method further includes a conformal polymer matrix disposed within the wells.

In an example of the fifth aspect, the conformal polymer matrix includes a polyacrylamide matrix.

In another example of the fifth aspect and the above examples, the polymer matrix is a cured-in-place polymer matrix.

In a further example of the fifth aspect and the above examples, the conformal polymer matrix is conjugated to an oligonucleotide.

In an additional example of the fifth aspect and the above examples, the well has a characteristic diameter in a range of 0.1 micrometers to 2 micrometers. In a further example of the fifth aspect and the above examples, the well has a thickness in a range of 0.01 micrometers to 10 micrometers.

In another example of the fifth aspect and the above examples, the plurality of sensors is ion-sensitive field effect transistors.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive- or and not to an exclusive- or. For example, a condition A or B is satisfied by any one of the following: A is true (or present) and B is false (or not present), A is false (or not present) and B is true (or present), and both A and B are true (or present).

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, may also be provided in combination in a single embodiment. Conversely, various features that are, for brevity, described in the context of a single embodiment, may also be provided separately or in any subcombination. Further, references to values stated in ranges include each and every value within that range.

What is claimed is:

1. A method of forming a polymer matrix array, the method comprising:
   treating a surface within a well of a well array with a surface compound including a surface reactive functional group and a radical-forming distal group;
   applying an aqueous solution including polymer precursors to the well of the well array; and activating the radical-forming distal group of the surface coupling compound with an initiator and atom transfer radical polymerization (ATRP) catalyst to initiate radical polymerization of the polymer precursors within the well of the well array to form the polymer matrix array.

2. The method of claim 1, wherein the surface reactive functional group includes phosphonate.

3. The method of claim 1, wherein the radical-forming distal group includes an amine or a hydroxyl group.

4. The method of claim 1, wherein the well has a characteristic diameter in a range of 0.1 micrometers to 2 micrometers.

5. The method of claim 1, wherein the well has a thickness in a range of 0.01 micrometers to 10 micrometers.

6. The method of claim 1, wherein wells of the well array overlie sensors of a sensor array, the wells corresponding to ion sensitive material of the sensors of the sensor array.

7. The method of claim 1, wherein the polymer precursors include a radically polymerizable monomer.

8. The method of claim 7, wherein the radically polymerizable monomer includes a vinyl-based monomer.

9. The method of claim 8, wherein the vinyl-based monomer includes acrylamide, vinyl acetate, hydroxyalkylmethacrylate, variations or derivatives thereof or any combination thereof.

10. The method of claim 1, wherein the polymer precursors include an oligonucleotide functionalized acrylamide.

11. The method of claim 1, wherein the polymer precursors include N-(5-bromoacetamidylpentyl)acrylamide.

12. The method of claim 1, wherein the polymer precursors include a crosslinker.

13. The method of claim 12, wherein the crosslinker is a bis-acrylamide.

14. A method comprising:
curing a polymer matrix within a well of an array of wells, the polymer matrix formed from precursors including an acrylate or an acrylamide and a bromine functionalized acrylate or acrylamide; and
applying a thiobenzamide oligonucleotide complex to the cured polymer, the thiobenzamide oligonucleotide complex reacting with the polymer matrix to form an oligonucleotide conjugated polymer matrix.

15. The method of claim 14, wherein the bromine functionalized acrylate or acrylamide include N-(5-bromoacetamidylpentyl)acrylamide.

16. The method of claim 14, wherein the acrylate or acrylamide includes hydroxyalkylacrylamide.

17. The method of claim 14, further comprising applying a target polynucleotide under amplification conditions to the oligonucleotide conjugated polymer matrix, wherein the oligonucleotide comprises sequences complementary to a portion of the target polynucleotide.

18. The method of claim 17, wherein the oligonucleotide is extended based at least in part on the target polynucleotide.

19. The method of claim 18, further comprising sequencing the extended oligonucleotide using a sensor operatively coupled to the well.

20. The method of claim 19, wherein sequencing includes sequentially applying solutions including nucleotides to the polymer matrix and measuring a response with the sensor.

* * * * *